(12) United States Patent
Egnelöv et al.

(10) Patent No.: US 7,654,963 B2
(45) Date of Patent: Feb. 2, 2010

(54) DEVICE FOR VISUALLY INDICATING A BLOOD PRESSURE

(75) Inventors: Per Egnelöv, Uppsala (SE); Fredrik Preinitz, Uppsala (SE); James Fuchs, Uppsala (SE); Dan Åkerfeldt, Uppsala (SE); Lars Tenerz, Uppsala (SE)

(73) Assignee: Radi Medical Systems AB, Uppsala (SE)

( * ) Notice: Subject to any disclaimer, the term of this patent is extended or adjusted under 35 U.S.C. 154(b) by 0 days.

(21) Appl. No.: 10/756,765

(22) Filed: Jan. 14, 2004

(65) Prior Publication Data

US 2004/0204654 A1 Oct. 14, 2004

Related U.S. Application Data

(60) Provisional application No. 60/439,800, filed on Jan. 14, 2003.

(51) Int. Cl.
*A61B 5/02* (2006.01)
*A61B 5/00* (2006.01)
*A61M 5/178* (2006.01)

(52) U.S. Cl. .................. 600/486; 600/485; 600/487; 600/561; 604/168.01; 604/900

(58) Field of Classification Search .............. 604/19, 604/48, 500, 506–510, 57, 59–64, 93.01, 604/164.13, 168.01, 513, 900; 606/213, 606/221; 600/481–489, 581, 561; 73/385, 73/748
See application file for complete search history.

(56) References Cited

U.S. PATENT DOCUMENTS

| | | | | |
|---|---|---|---|---|
| 2,748,769 A | * | 6/1956 | Huber | 604/272 |
| 3,062,202 A | * | 11/1962 | Hyman et al. | 600/487 |
| 3,730,168 A | * | 5/1973 | McWhorter | 600/561 |
| 4,767,408 A | | 8/1988 | McFarlane | |
| 4,894,052 A | * | 1/1990 | Crawford | 604/507 |
| 5,246,426 A | * | 9/1993 | Lewis et al. | 604/168.01 |
| 5,295,969 A | | 3/1994 | Fischell et al. | |
| 5,306,254 A | | 4/1994 | Nash et al. | |
| 5,342,393 A | * | 8/1994 | Stack | 606/213 |
| 5,431,639 A | | 7/1995 | Shaw | |
| 5,620,461 A | * | 4/1997 | Van De Moer et al. | 606/213 |
| 5,855,559 A | | 1/1999 | Van Tassel et al. | |
| 6,045,569 A | | 4/2000 | Kensey et al. | |
| 6,193,670 B1 | * | 2/2001 | Van Tassel et al. | 600/486 |
| 6,485,428 B1 | * | 11/2002 | Enk | 600/487 |
| 6,524,277 B1 | * | 2/2003 | Chang | 604/164.02 |

(Continued)

FOREIGN PATENT DOCUMENTS

EP 0 655 259 A2 5/1995

(Continued)

*Primary Examiner*—Patricia C Mallari
(74) *Attorney, Agent, or Firm*—Foley & Lardner LLP

(57) ABSTRACT

An indicator device for visually indicating a pressure of blood inside a blood vessel includes: a body, the body comprising a duct extending in the body and having a sealed proximal end; a distal end portion adapted to be positioned inside the blood vessel and including a liquid inlet opening in fluid communication with the duct; and a window including an at least semi-transparent section configured to enable visual observation of blood entering into the duct via the inlet opening when the inlet opening is located inside the blood vessel.

18 Claims, 9 Drawing Sheets

U.S. PATENT DOCUMENTS 6,689,070 B2 * 2/2004 Hung et al. .................. 600/562
6,794,485 B2 * 9/2004 Shalaby et al. .............. 528/354

FOREIGN PATENT DOCUMENTS

| EP | 0 858 776 A2 | 8/1998 |
| JP | 50-139588 | 11/1975 |
| JP | 3-170126 A | 7/1991 |

* cited by examiner

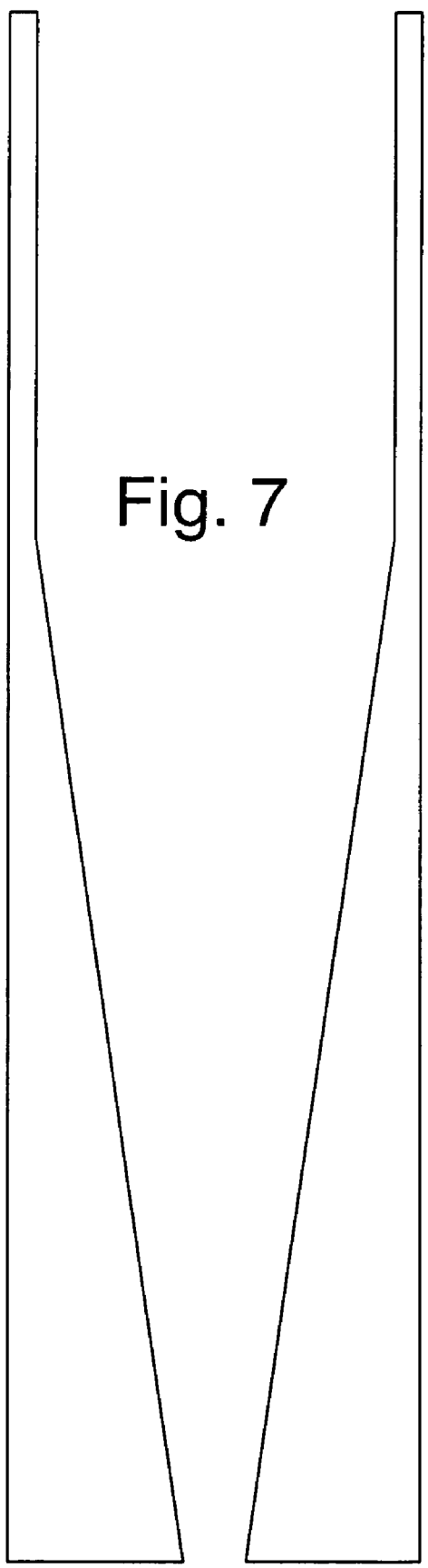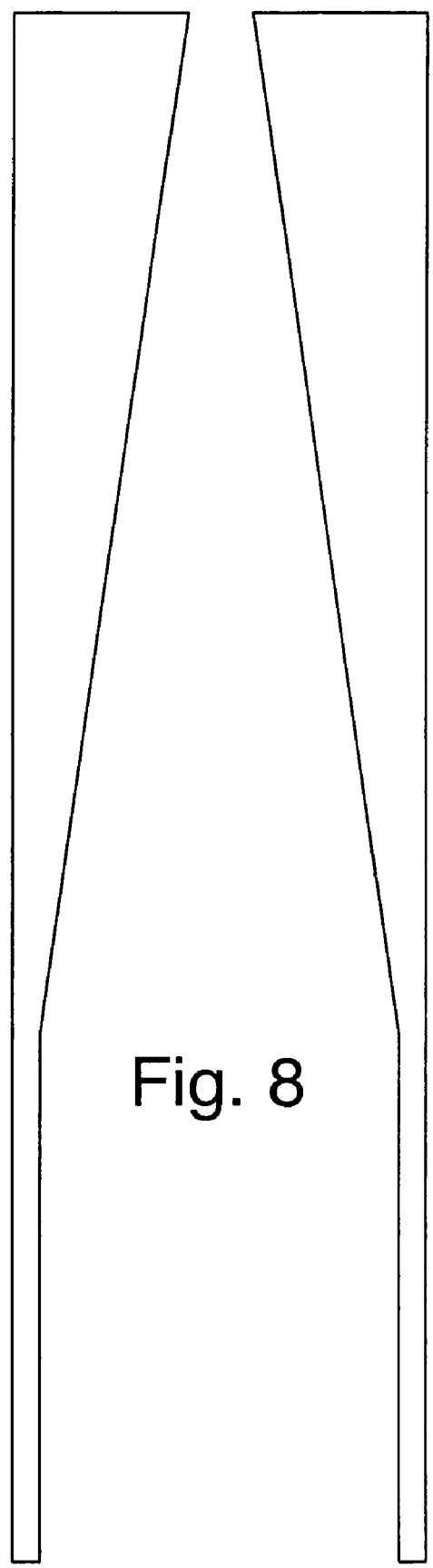

DEVICE FOR VISUALLY INDICATING A BLOOD PRESSURE

CROSS-REFERENCE TO RELATED PATENT APPLICATIONS

The present application claims priority to U.S. Provisional Application No. 60/439,800, filed on Jan. 14, 2003, the contents of which are hereby incorporated by reference.

FIELD OF THE INVENTION

The present invention relates to an indicator device for visually indicating a pulsating pressure of blood flowing inside a blood vessel, and a method, the device and method being usable for verifying correct positioning of an insertion tube for a wound closure element and of the wound closure element itself inside the blood vessel, in the process of closing a puncture in the blood vessel.

BACKGROUND OF THE INVENTION

A system for sealing a percutaneous puncture in a vessel can comprise an inner seal, which is adapted to be positioned against an inner surface of the vessel wall, and a locking member, which is connected to the inner seal by, for example, a filament or a suture and which is adapted to be positioned against an outer surface of the vessel wall, such that the percutaneous puncture is sealed there between. During the phase of inserting the inner seal, the inner seal is folded inside an insertion tube, resting in the puncture to provide access to the inner surface of the blood vessel. Deployment of the inner seal inside the vessel takes place by pushing the inner seal through the insertion tube, and out from its distal end opening. To ensure proper unfolding of the inner seal inside the vessel, the inner seal has to be Deployed some distance away from the puncture hole in the vessel wall before the inner seal is retracted to be securely seated against the inner surface of the vessel wall. When the inner seal has been deployed inside the blood vessel, the insertion tube is retracted out from the puncture, and in the same movement the inner seal is retracted and seated against the inner wall of the blood vessel. When the inner seal has been correctly positioned against the inner surface of the vessel wall, the locking member is pushed forward through the insertion tube until the locking member is in contact with the outer surface of the vessel wall. To effectuate the different actions described above, insertion tools have been proposed, which also accommodate the inner seal and the locking member before the sealing procedure.

As indicated, a critical moment in the above procedure is to ascertain a correct Positioning of the insertion tube before deployment of the inner seal. To achieve this there are various methods disclosed in the prior art. One method (see, e.g., U.S. Pat. No. 5,306,254) comprises making available a channel for blood to flow in through a distal opening in a dilator, inserted in an introducer sheath, via an opening or port located at a point on said introducer. There is also provided a proximal opening through which blood can flow out, whereby the occurrence or non-occurrence of outflow of blood indicates correct or incorrect position. Thereby, said port is located on the introducer sheath such that blood enters said port only when the tip of the introducer sheath is at a correct position. This method, although being relatively efficient, entails spillage of blood, which is inconvenient and may soil the environment around the patient to an undesirable extent.

In U.S. Pat. No. 5,295,969 there is disclosed a means for accessing blood vessels for the Insertion of a guide wire while preventing the free release of blood. Specifically, a hollow, thin-walled metal tube typically having a sharp point at its distal end is joined at its proximal end to a transparent viewing section. The viewing section has a distal narrow lumen and a proximal chamber which has a cap at its proximal end. The cap encloses a pressure sealing means through which a guide wire can be passed. After the distal end of the metal tube is placed in an artery, blood will rush through the metal tube and into the viewing section. The air in the air-tight proximal chamber will alternatively be compressed between diastolic and systolic blood pressure. Feedback to the operator that the distal end of the metal tube is properly placed within an artery can be achieved by observing the reciprocating pulsatile motion of the blood column within the distal narrow lumen of the viewing section. When the proper pulsatile motion is observed, a guide wire can be passed through the sealing means in the cap, through the viewing section, through the metal tube and finally the guide wire will enter the lumen of the artery.

However, a disadvantage with this device is that it will not be usable for all possible pressures that may be encountered. Namely, if blood enters the chamber the meniscus of blood will be located inside the chamber, and fluctuations may not readily be observed, either because the difference in levels between fluctuations is too small, or because the chamber simply cannot be observed.

SUMMARY OF THE INVENTION

The present invention aims to solve at least one of these and other problems.

An object of the present invention is therefore to provide a means for visual Indication that an insertion tube for a wound closure has been correctly positioned inside a blood vessel (i.e., verification of correct position), such that the closure element can be deployed safely and correctly, and whereby less blood flows from the puncture wound than compared to prior art procedures.

The device is usable together with a system for deploying and attaching a wound closure member, said device being connectable to an insertion tube of such a system, such that blood from a blood vessel in which the insertion tube is inserted can flow into the display device, for visually displaying the pulsation of the blood flowing into the device, thereby providing the desired verification.

According to a preferred embodiment of the present invention, an indicator device for visually indicating a pressure of blood inside a blood vessel may comprise: a body, the body comprising a duct extending in the body and having a sealed proximal end; a distal end portion adapted to be positioned inside the blood vessel and comprising a liquid inlet opening in fluid communication with the duct; and a window comprising an at least semi-transparent section configured to enable visual observation of blood entering into the duct via the inlet opening when the inlet opening is located inside the blood vessel.

According to another preferred embodiment of the present invention, a system for sealing a percutaneous wound in a blood vessel may comprise: an inner seal adapted to be positioned against an inner surface of a vessel wall of the blood vessel and a locking member connected to the inner seal and adapted to be positioned against an outer surface of the vessel wall, such that the percutaneous puncture is sealed therebetween; a body portion having at least one duct for insertion and extraction of devices to and from an inner region of said blood vessel; an insertion tube coupled to said body portion, and adapted to be inserted into the blood vessel through said wound, and through which the inner seal can be passed for deployment inside the blood vessel; and an indicator device for visually indicating a pressure of blood inside said blood vessel, comprising an indicator body, the indicator body comprising: an indicator duct extending in the indicator body and having a sealed proximal end; a distal end portion adapted to be positioned inside the blood vessel and comprising a liquid inlet opening in fluid communication with the indicator duct; and a window in the form of an at least semi-transparent section configured to enable visual observation of blood entering into the indicator duct via the inlet opening when the inlet opening is located inside the blood vessel.

According to a preferred embodiment of the present invention, a method for visually indicating a pressure of blood inside a blood vessel may comprise: providing an indicator device comprising a body, the body comprising a duct extending in the body and having a sealed proximal end, a distal end portion adapted to be positioned inside the blood vessel and comprising a liquid inlet opening in fluid communication with the duct, and a window in the form of an at least semi-transparent section configured to enable visual observation of blood entering into the duct via the inlet opening when the inlet opening is located inside the blood vessel; positioning said distal end portion inside the blood vessel; and indicating said pressure.

BRIEF DESCRIPTION OF THE DRAWINGS

The invention will now be further illustrated with reference to the attached drawings described below:

FIG. 7 schematically shows one embodiment of a duct with varying cross-section;

FIG. 8 schematically shows another embodiment of a duct with varying cross-section;

DETAILED DESCRIPTION OF PREFERRED EMBODIMENTS

Figure 1:
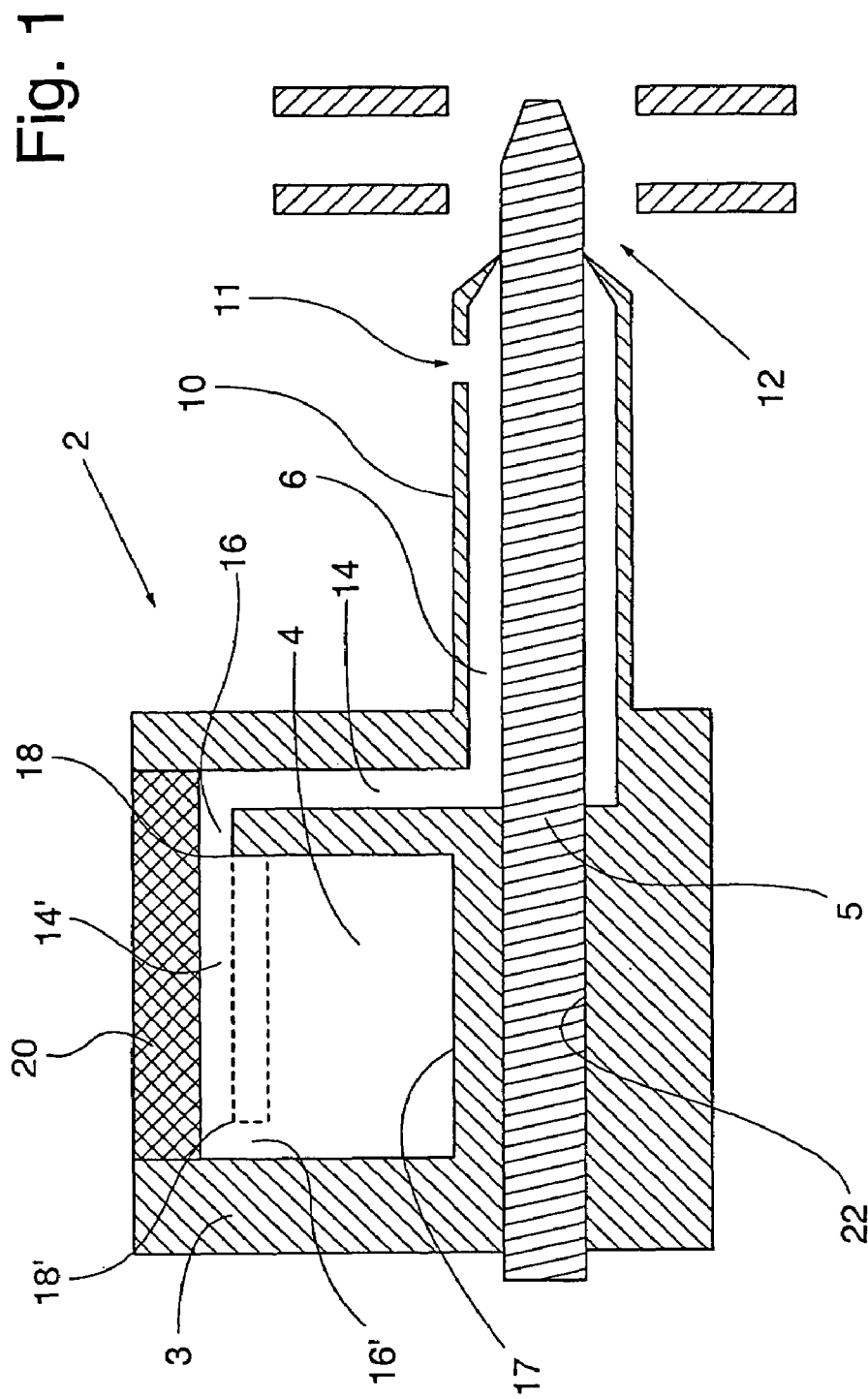
FIG. 1 schematically shows a system for deploying a wound closure including an indicator device according to the invention in an initial stage of the procedure.

An indicator device for visually indicating a pressure of blood flowing inside a blood vessel according to the present invention, in its most general aspect, comprises a structure that, as an example, can be provided in the form of a body or handle to be gripped by a user of the device, inside which a duct extends. The duct has a distal end and a proximal end. A liquid inlet opening is provided at the distal end of the overall structure in fluid communication with the duct. The duct can extend all the way up to the distal end of the structure. The proximal end is sealed, such that no gas or liquid can escape from the duct at the proximal end. The distal end portion of the structure is adapted to be positioned inside the blood vessel. The inlet opening can be provided at the very distal tip of the distal end portion of the structure, or at a preferably known distance from the tip. The distal portion of the structure can be shaped as a tube which can have a suitable diameter for being inserted into the blood vessel, which will be described more in detail below. By shaping the structure as a tube in this region, and by providing the inlet opening on the tube in the distal region thereof, also the inlet opening can be positioned inside the blood vessel. The tube can be provided as a separate part that is attachable to the body, or it could be integrated with the body to form a unitary structure. The structure has an at least semi-transparent section, forming a wall or a window in the duct, for enabling visual observation of liquid entering into the duct via the inlet opening, when the inlet opening is located inside the blood vessel.

Due to the over-pressure in a blood vessel, i.e., higher than the atmospheric pressure, blood entering the duct when the device is properly deployed inside the blood vessel will flow into the duct, via the inlet opening, until the gas pressure inside the sealed system counterbalances the blood pressure, and when the blood goes through the pulsation cycle with diastolic and systolic pressures, the meniscus in the duct will oscillate correspondingly between two levels or positions in the duct.

One embodiment of the invention comprises a relatively long, say up to 1 meter (or at least a few decimeters long), narrow diameter tubing, the diameter of which suitably is 0.5-2 mm, more preferably 1-1.5 mm. In this embodiment the tubing itself constitutes the "structure," according to the general concept mentioned above, and the lumen inside the tubing constitutes the duct. Suitably there is provided a support member for gripping the device as a whole, on which support member a support element can be attached. The tubing suitably is wound around the support element to form a helical structure, in order to reduce the length/size of the "window" for visual inspection of the pulsating blood. Due to the narrow dimension of the tubing, blood flowing inside the tubing from a blood vessel in which the pressure is slightly higher than atmospheric will be easily perceptible as it fluctuates or oscillates between two levels in the helix, similar to what was described above.

In a preferred embodiment, schematically illustrated in FIG. 1 (which shows a device according to the invention integrated in a system for deployment of a wound closure element, in an initial state before being inserted into a blood vessel), the device according to the invention, generally designated 2, comprises a main body 3 in which there is a gas-filled container or chamber/cavity 4 coupled via a fluid communication pathway 6 to the blood vessel 8. The body 3 has a protruding member in the form of an insertion tube 10 having a diameter rendering it suitable for insertion through a percutaneous wound 12 in the blood vessel 8. The tube 10 is provided with a liquid inlet opening 11 for enabling blood to flow into the fluid communication pathway 6, when the insertion tube 10 is located inside the blood vessel 8. In the fluid communication pathway 6 there is provided a narrow duct 14, entering via an aperture 16 into the chamber 4 at a level above the lowest level, i.e., the bottom 17, of the chamber 4, thereby creating a spill-over edge 18 for blood exiting through the aperture 16. In the shown embodiment the duct 14 extends essentially vertically and is located above the chamber 4, whereby gravity will cause the excess blood to drop down into the chamber 4.

In FIG. 1 there is also inserted a guide rod 5 in the pathway 6, the function of which is to make insertion of the device into the blood vessel 8 easier. This guide rod 5 is subsequently removed when the correct position of the deployment device has been attained and verified using the present invention. After removal the wound closure device can be inserted, deployed and attached.

In a preferred embodiment the duct 14' extends preferably essentially horizontally in the upper region of the main body 3 (indicated by broken lines in FIG. 1; shown with solid lines in FIGS. 2-8) to an opening 16' and a spill-over edge 18'. A window 20 (shown by cross-hatching) formed by making the body 3 at least semi-transparent in this essentially horizontal region enables visual observation of blood flowing in the duct.

The gas-filled chamber 4 is normally, i.e., in non-operative condition, at atmospheric pressure, and the gas will normally be air, although other gases are possible.

In particular the device according to the invention is usable together with a system for the safe and correct deployment and positioning of an inner seal of a sealing unit for closing a percutaneous puncture in a blood vessel, whereby the device according to the invention will be used for verification of correct positioning of parts of the system before the inner seal of a wound closure device is deployed inside the vessel.

A blood vessel sealing unit can comprise an inner seal, which is adapted to be positioned against an inner surface of the blood vessel wall, and a locking member, which is connected to the inner seal by, for example, a filament or a suture and which is adapted to be positioned against an outer surface of the blood vessel wall, such that the percutaneous puncture is sealed there between.

In order that the inner seal shall be capable of covering the puncture, it must have an extension that is larger than the hole. Therefore it must be folded together during passage of the hole, and it must be deployed at a minimum distance from the vessel wall inside the vessel. The inner seal is passed through the hole via an insertion tube (corresponding to the tube 10 in FIG. 1, however the guide rod 5 shown in FIG. 1 must of course have been removed in order that this is possible), and when it exits the insertion tube at the distal end thereof, it unfolds. A preferred distance for deployment, although not limited thereto, is about 10-20 mm from the vessel wall. In order to enable deployment at this preferred position, the inventors have devised the position indicator means according to the present invention, which thus can be coupled to the insertion system/device.

A system/device for the insertion/deployment of an inner seal of a wound closure unit, together with which the invention can be used, generally comprises a body (corresponding to the body 3 shown in FIG. 1) provided with at least one passage/lumen/channel 22 for passing devices such as a guide wire (not shown), a guide rod 5 or a dilator (not shown) in and out of the blood vessel 8 (only one of these devices are shown in FIG. 1, namely a guide rod 5). An insertion tube 10 can be a separate member coupled to the body 3 such that it attaches to an outlet of the passage/lumen/channel 22 (although in FIG. 1 it is shown as an integrated part of the body 3). The indicator device 2 according to the invention is preferably integrated in the body 3. It comprises a cavity or chamber 4 inside the body for the accommodation of blood. The chamber 4 is in fluid communication with the blood vessel 8 via the insertion tube 10. Thus, when the insertion tube 10 is located inside the blood vessel 8, the pressure difference will force blood to flow into the insertion tube 10, via the duct 14, 14' and enter into the cavity 4 in the body 3. However if the blood pressure is low, the blood might not reach all the way to the chamber 4, but will only extend in the duct 14, 14' to some position where it may be observed through the window 20.

The function of an indicator device 2 according to the invention will now be described with reference to the embodiment shown in FIGS. 1-6.

The embodiment of the indicator device 2 according to the invention shown in FIGS. 1-6 is integrated with a system for insertion/deployment of an inner seal of a wound closure unit, schematically illustrated in FIG. 1, which shows an initial state just before the distal end of the insertion tube 10 is inserted into the blood vessel 8. The guide rod 5 is inserted and extends out from the insertion tube 10 so as to provide for easy entry into the blood vessel 8 through the wound 12. In this stage no blood flows into the side opening 11 in the insertion tube 10.

Figure 2:
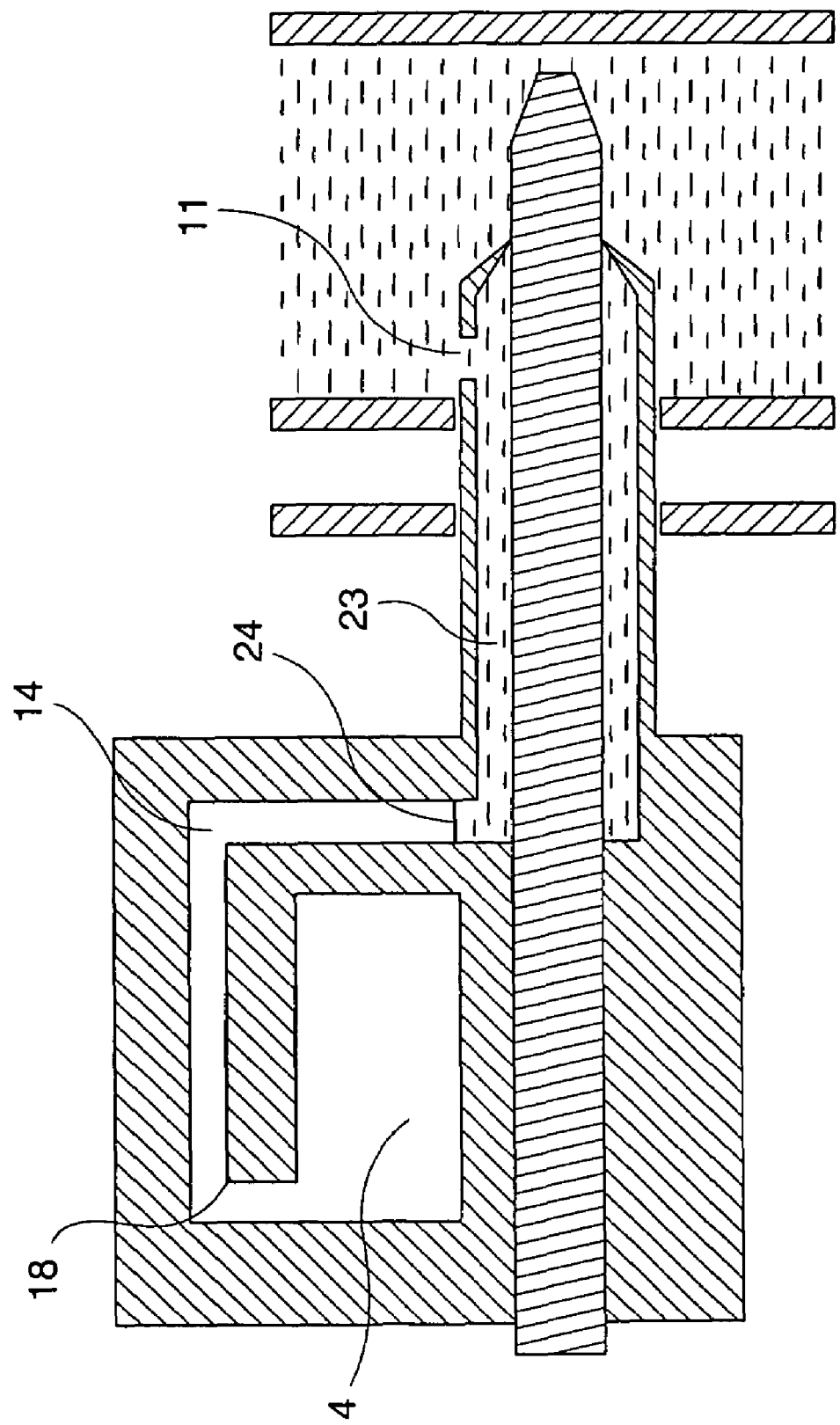
FIG. 2 shows the system of FIG. 1 in a situation wherein the indicator detects a diastolic pressure.

In FIG. 2 the insertion tube has been inserted into the blood vessel 8 to a point where blood 23 can enter the side opening 11. The situation in FIG. 2 corresponds to a situation in the heart (pulse) cycle where diastolic pressure prevails. In this case, the air inside the chamber 4 is slightly compressed but the blood pressure is not high enough to enable the blood 23 to flow all the way into the chamber 4. Instead the meniscus 24 is positioned at a distance from the spill-over edge 18.

Figure 3:
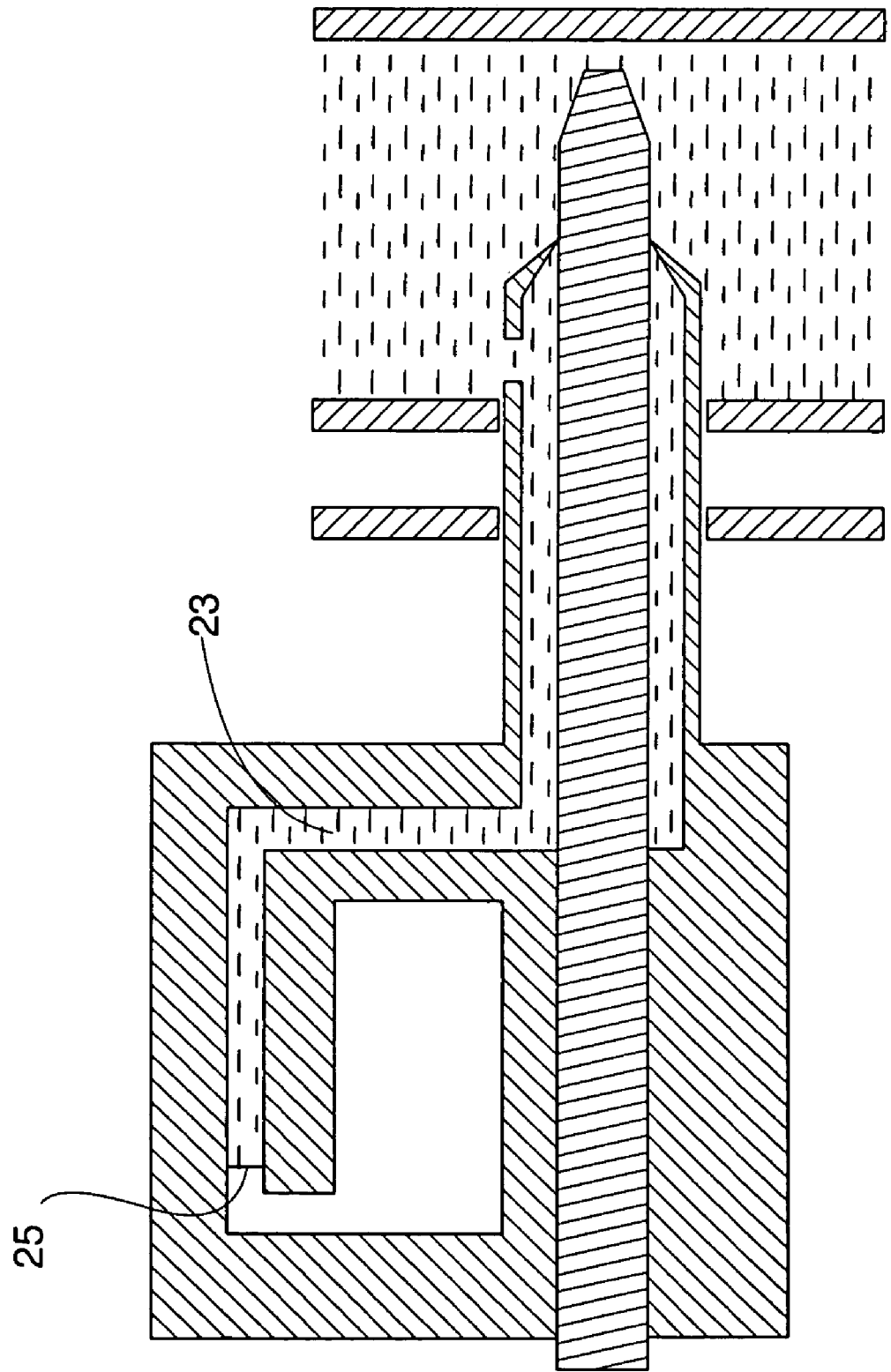
FIG. 3 shows the system of FIG. 1 in a situation wherein the indicator detects a systolic pressure.

Next in FIG. 3, a situation corresponding to systolic pressure is illustrated. Here, the blood has flowed in the duct 14 all the way up to the spill-over edge 18', but has not actually flowed into the chamber 4. Thus, the meniscus 25 is located near the edge 18'.

Figure 4:
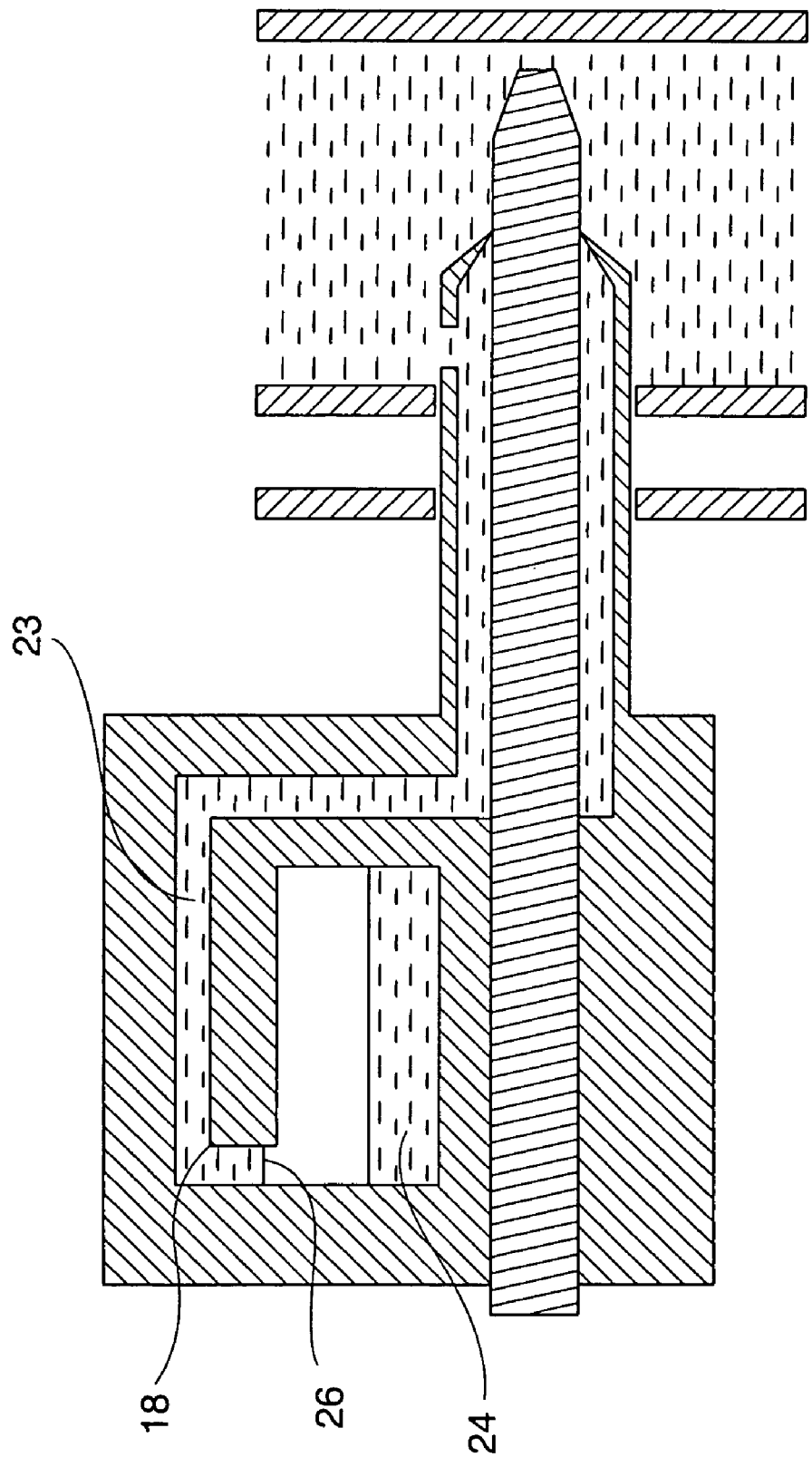
FIG. 4 shows the system of FIG. 1 in a situation wherein the indicator detects a high systolic pressure.

In FIG. 4 on the other hand, the systolic pressure is high enough that the blood has flowed over the spill-over edge 18', and dropped down into the chamber 4, where a pool 24 of blood collects. Blood 23 will continue to flow over the edge 18' until the pressure inside the chamber 4 counterbalances the blood pressure. Then, when the pressure returns to diastolic, the meniscus 26 will withdraw to a position that could resemble the one shown at 27 in FIG. 5.

By providing the spill-over edge 18, 18' such that it always will be located over the level of blood 23 collecting in the blood accommodating chamber 4, return flow back into the duct 14 will be prevented.

Figure 6:
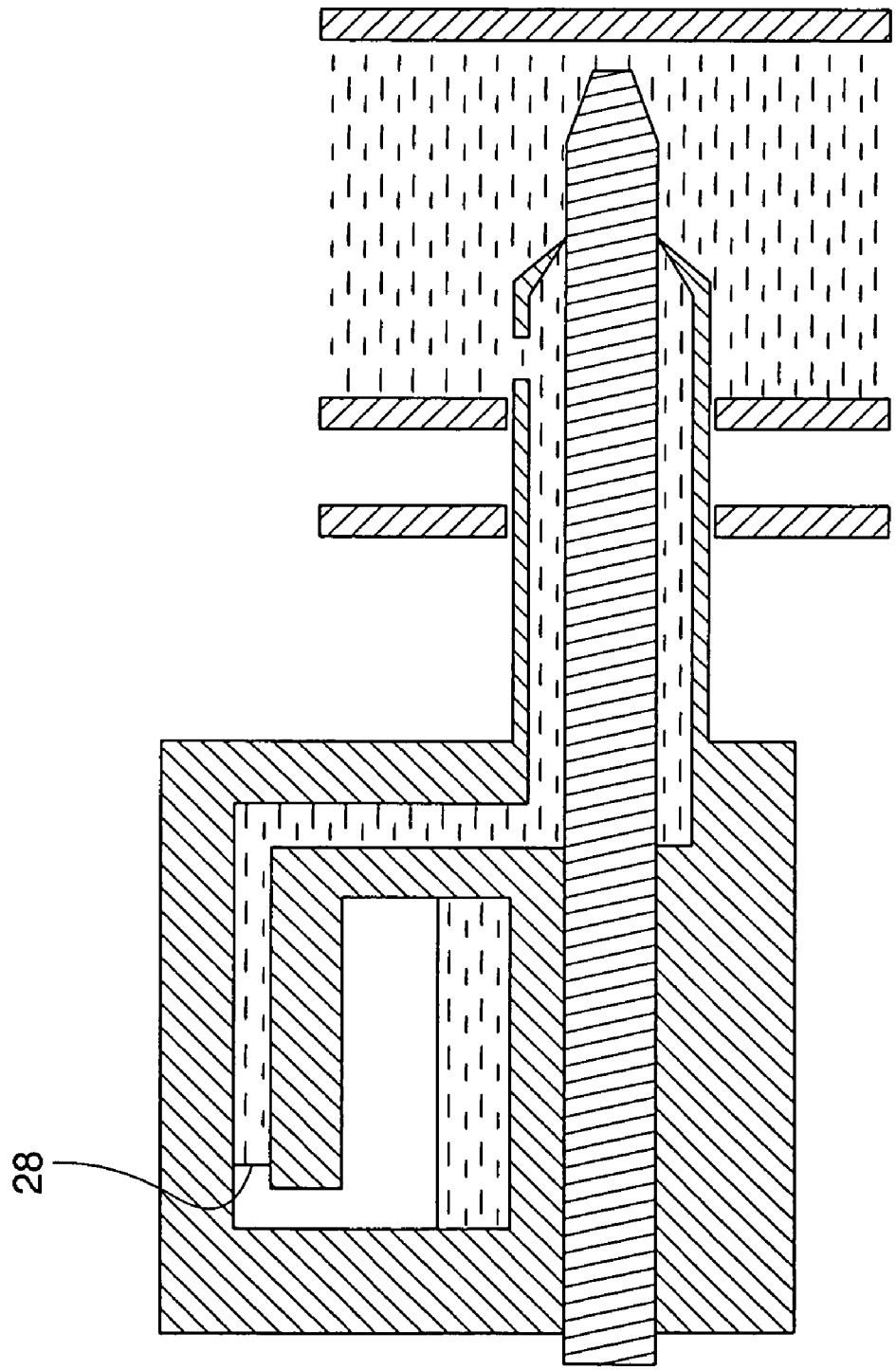
FIG. 6 shows the system of FIG. 1 in a situation wherein the indicator detects a systolic pressure after calibration.

In the next cycle, when the pressure returns to systolic again, as shown in FIG. 6, the meniscus 28 will again attain the same position as shown in FIG. 3.

In an optimized configuration, the chamber volume is adapted to the expected pressure ranges (systolic pressure ranges approximately between 100-200 mm Hg, and diastolic pressure ranges approximately between 60-100 mm Hg), such that the lowest possible (or imaginable) systolic pressure (i.e., about 100 mm Hg) would render the meniscus of the blood in the duct 14 visible in the window 20 of the device. Preferably it would extend up to or close to the spill-over edge 18, 18'.

Similarly, the highest diastolic pressure (i.e., about 100 mm Hg) should not extend too far into the window 20, and could even be invisible through the window 20. In the latter case, however, the lowest possible systolic pressures would not either be visible in the window 20, and thus a balance between these two situations must be ascertained.

Set up in this way, all pressures that may be encountered during a detection procedure would be visually detectable. High systolic pressures would lead to the blood flowing over the spill-over edge 18, 18' until a counter pressure inside the blood accommodating chamber 4 will prevent further flow. Again, it should be emphasized that the arrangement of the spill-over edge 18, 18' relative to the chamber 4 will prevent return flow into the duct 14.

The key to achieving proper function is therefore to dimension the duct 14 and chamber 4 appropriately. This would be a matter of experimentation that is within the ability of the skilled artisan.

Figure 5:
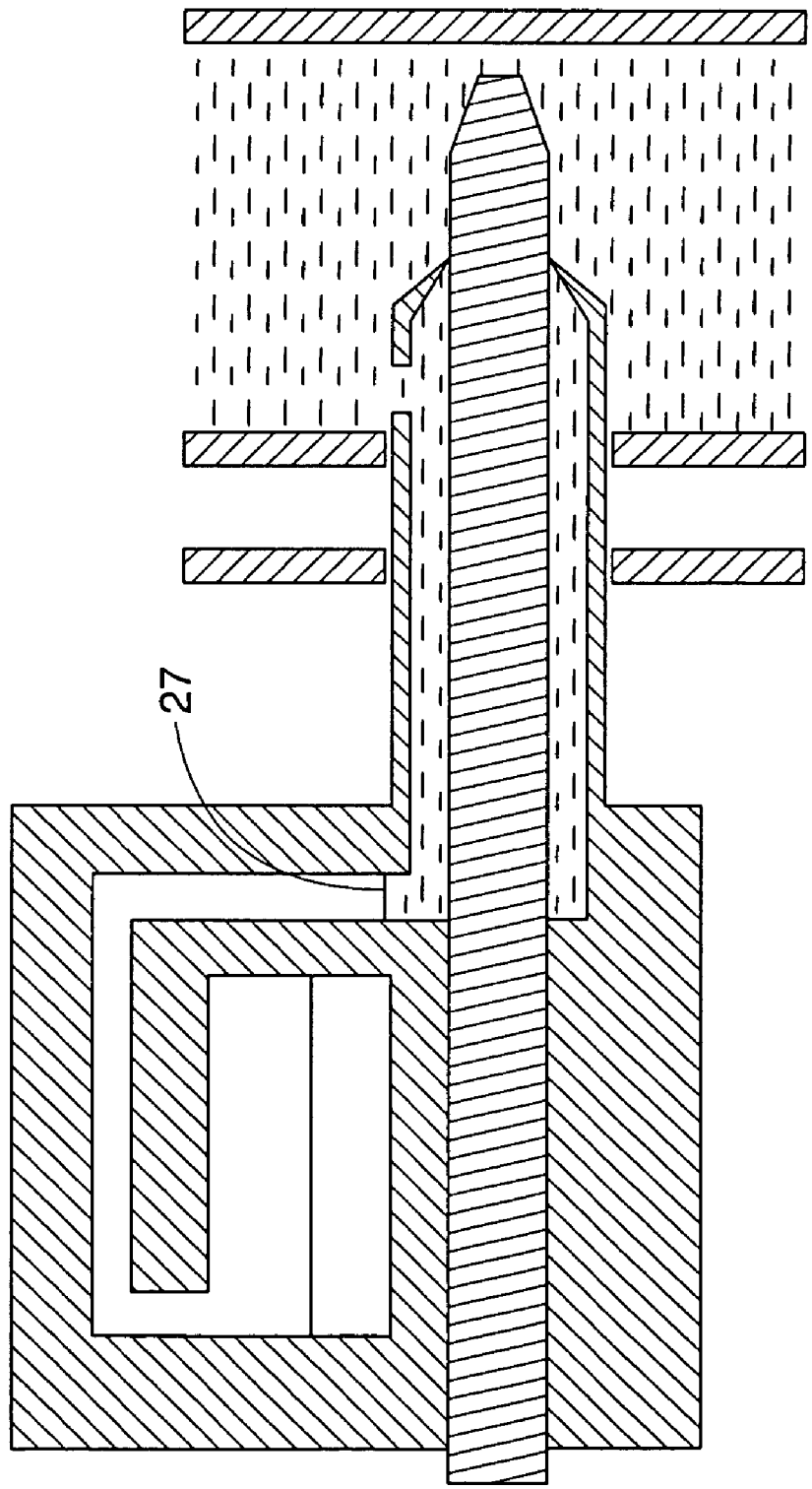
FIG. 5 shows the system of FIG. 1 in a situation wherein the indicator detects a diastolic pressure after calibration.

One operable embodiment that has been tested has a chamber volume of about 620 mm$^3$, and a volume of the duct 14 of about 80 mm$^3$, as measured from the exit into the chamber 4 (near the spill-over edge 18, 18') and to a point corresponding to the location of the blood meniscus 27 as shown in FIG. 5. These values are of course only exemplary, and are not to be construed as limiting on the invention, which can be varied in many ways.

The cycle described above that the system goes through is in effect a self-calibration of the device to set itself up for displaying the meniscus through the window 20 in the body 3, in a state of systolic pressure, and to at least partially withdraw from sight in the window 20 during diastolic pressure. The self-calibration is an effect of the relative arrangement of the spill-over edge 18, 18' and the chamber 4, respectively.

For the intended use together with a system for deployment of an inner seal of a wound closure unit, it is preferable if the inner seal can be deployed at a distance of at least about 10 mm from the puncture or vessel wall, in order that the seal be able to unfold properly, before it is retracted to rest against the wall.

To this end, the inlet opening 11 is positioned at a distance of about 10 mm from the tip of the insertion tube 10. Thereby, the operator will immediately recognize when the correct position has been reached because he will immediately be able to observe a fluctuating meniscus of blood 23 through the window 20. Should the device inadvertently be retracted such that the tip of the insertion tube 10 no longer is at the desired distance, this will also immediately be registered by the terminated fluctuations of blood 23 in the window 20.

In another preferred embodiment of the invention, the duct 14 can have a varying cross-section over its length. The reason for this is that it will be possible to amplify small pressure variations in the beginning of a heart cycle. Namely, by making the duct 14 narrower in the first part, say corresponding to the vertical portion of the duct 14 seen in FIG. 1, or say half of the horizontally extending portion of the duct 14' in FIG. 1, it will be possible to more easily detect a very slight pressure increase. The cross-section can be changed stepwise along the duct 14 or continuously changed. The detailed design of the profile of the changing cross-section for a desired purpose can be arrived at with routine experimentation.

Alternatively, the duct 14 can be made to continuously become narrower towards the spill-over edge 18, 18' (towards blood accommodating chamber 4), whereby the sensitivity in the detection of pulsation is varied. Also, by shaping the duct 14 suitably, i.e., to account for the varying pressure during a cycle, a linear displacement of blood 23 within the window 20 can be achieved. This can be of advantage if the fluctuations are large in or near the systolic pressure region and smaller in other pressure ranges. These alternative designs are shown schematically in FIGS. 7-9.

Another option is to let the duct 14 widen in the direction towards the spill-over edge 18, 18' (towards blood accommodating chamber 4). Widening can be more forgiving, in the sense that it can accommodate a wider pressure range.

Figure 9:
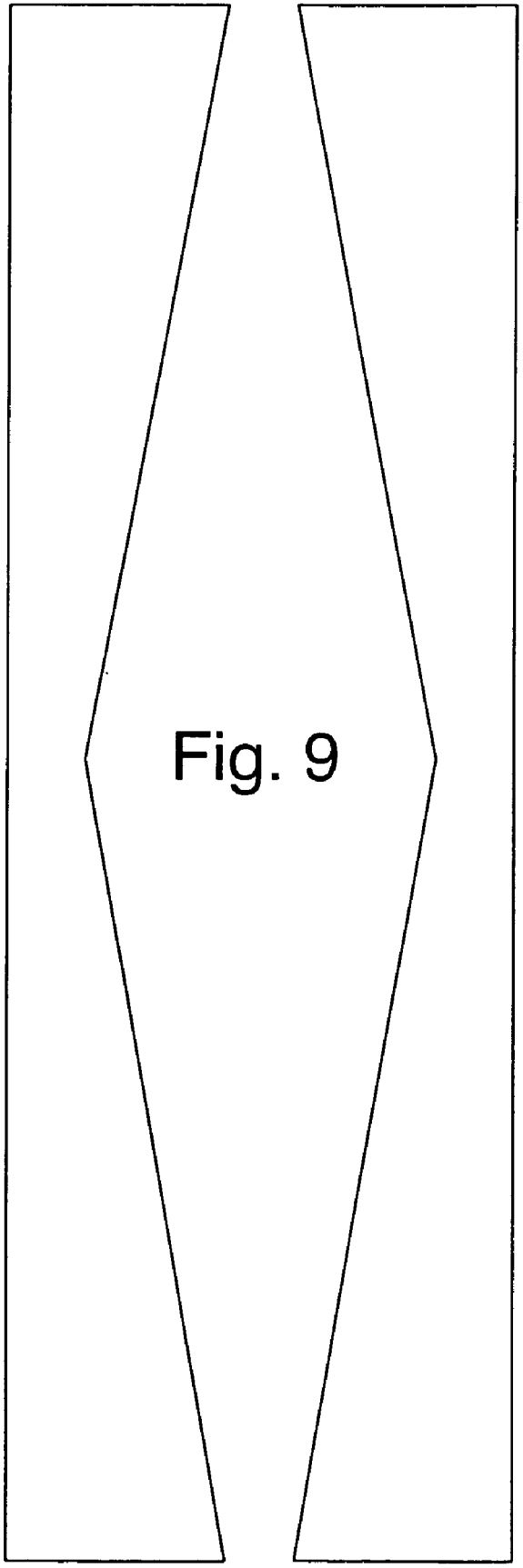
FIG. 9 schematically shows a further embodiment of a duct with varying cross-section.

In fact, it would also be possible to arrange parallel ducts having inverted variations of the cross-section, so as to ascertain detection in both cases mentioned. In another embodiment the duct 14 could be made to widen in a first region, and than become narrower in a second region, as shown in FIG. 9.

A further preferred embodiment comprises a duct 14 having such dimensions that the meniscus of the blood 23 flowing in the duct 14 always will be essentially perpendicular to the direction of flow. This would be achieved by making the duct 14 thin enough, such that capillary forces will maintain the desired perpendicularity of the meniscus. Suitably the duct 14 is 2-3 mm thick or less, more preferably the duct 14 is 1 mm thick or less, most suitably 0.5 mm or less. A suitable width of the duct 14 in the window 20 could be about 1-5 mm, preferably 2-4 mm, although other dimensions could equally well be suitable for specific purposes.

Figure 10:
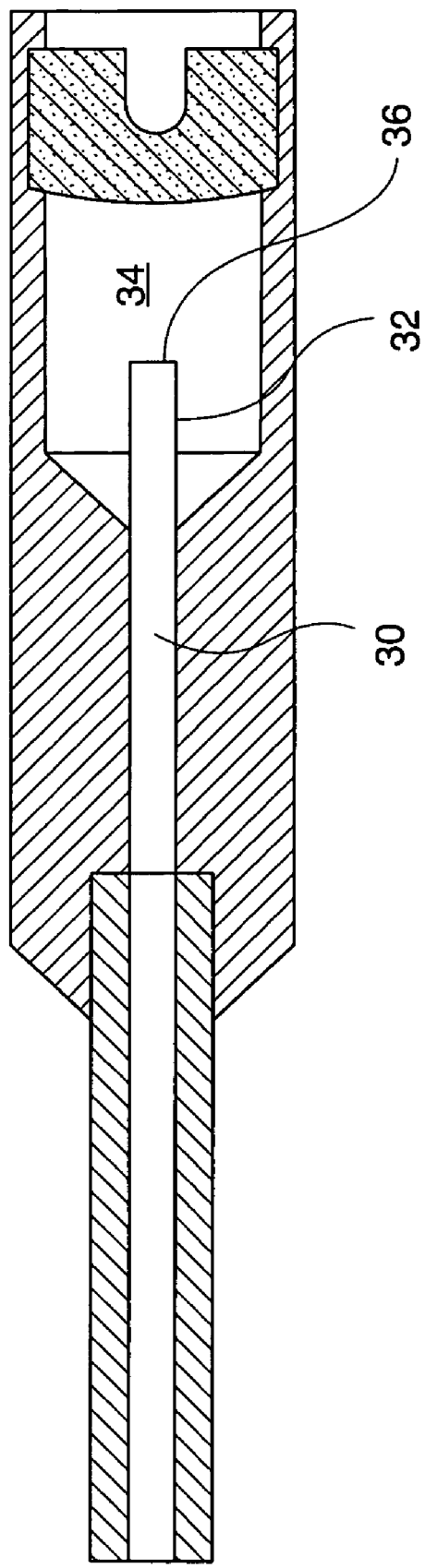
FIG. 10 schematically shows a further embodiment of a device according to the invention.

In an alternative embodiment of the device according to the invention, schematically shown in FIG. 10, the prior art device shown in U.S. Pat. No. 5,295,969 can be modified according to the present invention, by extending the lumen 30, by providing a piece of tubing 32 extending into the blood accommodating chamber 34. The proximal opening of the tube 32 will form a spill-over edge 36. In this way, the device will be rotationally symmetric, and the orientation during insertion of the needle into a blood vessel is unimportant.

In actual practice of using a system for wound closure, together with which the invention is primarily intended to be used, the insertion tube 10 is normally inserted into the blood vessel at an angle of say 30-45° with respect to the extension of the blood vessel in question. In a situation like that, it can be advantageous if there are provided two oppositely located inlet openings 11 on the insertion tube 10. The two openings will then be located at different distances from the tip of the insertion tube 10. The difference is such as to render the position of both openings essentially the same, with respect to the inner vessel wall, when the insertion tube is inserted into the blood vessel at the mentioned angle. The two openings are provided as a measure to ascertain that at least one of them will be exposed to the blood inside the vessel.

What is claimed is:

1. An indicator device for visually indicating a pressure of blood inside a blood vessel, comprising:
   a body comprising a passage passing through the body, the body further comprising a duct extending in the body and having a hemostatically sealed blood accommodating chamber;
   an insertion tube comprising a distal end adapted to be positioned inside the blood vessel and comprising a fluid communication pathway between an uncovered liquid inlet opening near a distal end of the insertion tube and the duct, wherein the inlet opening is formed on an outer surface of the insertion tube, the insertion tube further comprising an opening at an extreme end of the distal end portion;
   a window comprising an at least semi-transparent section configured to enable visual observation of blood entering into the duct via the inlet opening when the inlet opening is located inside the blood vessel; and
   an elongated member;
   wherein the fluid communication pathway is formed between the insertion tube and the elongated member;
   and wherein the body and the insertion tube are adapted to permit the elongated member to be threaded in a substantially straight path there through between the distal end of the insertion tube and a proximal end of the body and wherein an outer dimension of the elongated member is substantially equal to an inner dimension of the insertion tube at the distal end of the insertion tube and said outer dimension and said inner dimension are configured such that flow of blood between said outer dimension and said inner dimension is prevented when the elongated member is inserted into the insertion tube.

2. The system as claimed in claim 1, wherein the elongated member comprises a guide wire.

3. The system as claimed in claim 1, wherein the duct opens into the chamber via an aperture having a spill-over edge, the aperture being located at a level above a bottom surface of the blood accommodating chamber, whereby return flow of blood back into the duct is prevented.

4. The system as claimed in claim 1, wherein the blood accommodating chamber is located in the body, and wherein the body further comprises the insertion tube extending distally of the body.

5. The system as claimed in claim 4, wherein the inlet opening is located on a side of the insertion tube.

6. The system as claimed in claim 1, wherein the duct extends vertically to an aperture opening into the blood accommodating chamber.

7. The system as claimed in claim 1, wherein the duct extends horizontally above the blood accommodating chamber to an aperture opening into the blood accommodating chamber.

8. The system as claimed in claim 1, wherein the duct exhibits a varying cross-section over its length.

9. The system as claimed in claim 1, wherein the indicator system is configured such that blood flows from a region outside of the insertion tube, through the inlet opening, and into an interior of the insertion tube.

10. The system as claimed in claim 9, wherein the indicator system is configured such that blood flows from a region outside of the insertion tube, through the opening at the extreme end of the distal end portion of the insertion tube, and into an interior of the insertion tube when the opening at the extreme end of the distal end portion of the insertion tube is not blocked.

11. The system as claimed in claim 1, wherein the elongated member is of a one-piece, solid construction.

12. The system as claimed in claim 1, wherein the indicator system is configured such that a portion of the outer surface of the insertion tube that forms the inlet opening is exposed to the blood vessel when the distal end portion of the insertion tube is positioned inside the blood vessel.

13. An indicator system for visually indicating a pressure of blood inside a blood vessel, comprising:
- a body comprising a passage passing through the body, the body further comprising a duct extending in the body and having a hemostatically sealed blood accommodating chamber;
- an insertion tube comprising a distal end portion adapted to be positioned inside the blood vessel and comprising a fluid communication pathway between an uncovered liquid inlet opening near a distal end of the insertion tube and the duct, further comprising an opening at an extreme end of the distal end portion of the insertion tube, wherein the inlet opening is formed on an outer surface of the insertion tube; and
- a window comprising an at least semi-transparent section configured to enable visual observation of blood entering into the duct via the inlet opening when the inlet opening is located inside the blood vessel; and
- an elongated member;
- wherein the fluid communication pathway is formed between the insertion tube and the elongated member;
- and wherein the body and the insertion tube are adapted to permit the elongated member to be threaded in a substantially straight path there through between the distal end of the insertion tube and a proximal end of the body such that the elongated member projects distally past the extreme end of the distal end portion and wherein an outer dimension of the elongated member is substantially equal to an inner dimension of the insertion tube at the distal end of the insertion tube and said outer dimension and said inner dimension are configured such that flow of blood between said outer dimension and said inner dimension is prevented when the elongated member is inserted into the insertion tube.

14. A method for visually indicating a pressure of blood inside a blood vessel, comprising:
(1) providing an indicator system comprising
- a body, the body comprising a passage passing through the body and a duct extending in the body and having a blood accommodating chamber,
- an insertion tube comprising a distal end portion adapted to be positioned inside the blood vessel and comprising a fluid communication pathway between a liquid inlet opening near a distal end of the insertion tube and the duct, wherein the inlet opening is formed on an outer surface of the insertion tube, the insertion tube further comprising an opening at an extreme end of the distal end portion,
- a window in the form of an at least semi-transparent section configured to enable visual observation of blood entering into the duct via the inlet opening when the inlet opening is located inside the blood vessel, and
- an elongated member,
- wherein the fluid communication pathway is formed between the insertion tube and the elongated member;
- and wherein the body and the insertion tube are adapted to permit the elongated member to be threaded in a substantially straight path there through between a proximal end of the body and the distal end of the insertion tube to plug the opening at the extreme end of the distal end portion;
(2) positioning said distal end portion inside the blood vessel; and
(3) indicating said pressure.

15. An indicator device for visually indicating a pressure of blood inside a blood vessel, comprising:
a body, the body comprising:
- a duct extending in the body and having a blood accommodating chamber at a hemostatically sealed proximal end;
- a distal end portion adapted to be positioned inside the blood vessel and comprising a liquid inlet opening in fluid communication with the duct; and
- a window comprising an at least semi-transparent section configured to enable visual observation of blood entering into the duct via the inlet opening when the inlet opening is located inside the blood vessel;
- wherein the duct opens into the chamber via an aperture having a spill-over edge, the aperture being located at a level above a bottom surface of the blood accommodating chamber, whereby return flow of blood back into the duct is prevented;
- wherein the blood accommodating chamber and the duct are dimensioned such that a counter-pressure therein when blood enters will cause a blood meniscus at a lowest possible systolic pressure to be located within the window;
- wherein the blood accommodating chamber and the duct are dimensioned such that a counter-pressure therein when blood enters will cause a blood meniscus at the lowest possible systolic pressure to be located approximately at the spill-over edge.

16. An indicator system for visually indicating a pressure of blood inside a blood vessel, comprising:

a body comprising a passage passing through the body, the body further comprising a duct extending in the body and having a hemostatically sealed blood accommodating chamber;

an insertion tube comprising a distal end portion adapted to be positioned inside the blood vessel and comprising a fluid communication pathway between an uncovered liquid inlet opening near a distal end of the insertion tube and the duct, the insertion tube further comprising an opening at the extreme end of the distal end portion; and a window comprising an at least semi-transparent section configured to enable visual observation of blood entering into the duct via the inlet opening when the inlet opening is located inside the blood vessel; and an elongated member;

and wherein the passage and the fluid communication pathway are adapted to permit the elongated member to be threaded in a substantially straight path there through between a distal end of the insertion tube and a proximal end of the body such that the elongated member projects distally past the extreme end of the distal end portion, wherein the blood accommodating chamber and the duct are dimensioned such that a counter-pressure therein when blood enters will cause a blood meniscus at a lowest possible systolic pressure to be located within the window.

17. An indicator system for visually indicating a pressure of blood inside a blood vessel, comprising:

a body comprising a passage passing through the body, the body further comprising a duct extending in the body and having a hemostatically sealed blood accommodating chamber;

an insertion tube comprising a distal end portion adapted to be positioned inside the blood vessel and comprising a fluid communication pathway between an uncovered liquid inlet opening near a distal end of the insertion tube and the duct, wherein the inlet opening is formed on an outer surface of the insertion tube, the insertion tube further comprising an opening at an extreme end of the distal end portion;

a window comprising an at least semi-transparent section configured to enable visual observation of blood entering into the duct via the inlet opening when the inlet opening is located inside the blood vessel; and an elongated member;

wherein the fluid communication pathway is formed between the insertion tube and the elongated member;

and wherein the body and the insertion tube are adapted to permit the elongated member to be threaded in a substantially straight path there through between the distal end of the insertion tube and a proximal end of the body;

wherein the elongated member comprises a guide rod and wherein an outer dimension of the guide rod is substantially equal to an inner dimension of the insertion tube at the distal end of the insertion tube and said outer dimension and said inner dimension are configured such that flow of blood between said outer dimension and said inner dimension is prevented when the guide rod is inserted into the insertion tube.

18. An indicator system for visually indicating a pressure of blood inside a blood vessel, comprising:

a body comprising a passage passing through the body, the body further comprising a duct extending in the body and having a hemostatically sealed blood accommodating chamber;

an insertion tube comprising a distal end portion adapted to be positioned inside the blood vessel and comprising a fluid communication pathway between an uncovered liquid inlet opening near a distal end of the insertion tube and the duct, wherein the inlet opening is formed on an outer surface of the insertion tube, the insertion tube further comprising an opening at an extreme end of the distal end portion;

a window comprising an at least semi-transparent section configured to enable visual observation of blood entering into the duct via the inlet opening when the inlet opening is located inside the blood vessel; and an elongated member;

wherein the fluid communication pathway is formed between the insertion tube and the elongated member;

and wherein the body and the insertion tube are adapted to permit the elongated member to be threaded in a substantially straight path there through between the distal end of the insertion tube and a proximal end of the body and wherein an outer dimension of the elongated member is substantially equal to an inner dimension of the insertion tube at the distal end of the insertion tube and said outer dimension and said inner dimension are configured such that flow of blood between said outer dimension and said inner dimension is prevented when the elongated member is inserted into the insertion tube;

wherein the elongated member comprises a dilator.

* * * * *